United States Patent [19]

Cornwell

[11] Patent Number: 5,203,458
[45] Date of Patent: Apr. 20, 1993

[54] CRYPTOPLATE DISPOSABLE SURGICAL GARMENT CONTAINER

[75] Inventor: James T. Cornwell, Cleveland, Tenn.

[73] Assignee: Quality Containers International, Inc., Cleveland, Tenn.

[21] Appl. No.: 844,177

[22] Filed: Mar. 2, 1992

[51] Int. Cl.⁵ .................. B65D 81/70; B65D 33/29
[52] U.S. Cl. .................. 206/524.8; 206/278; 206/438; 383/62; 383/100
[58] Field of Search .......... 206/438, 440, 524.8, 206/278, 439; 383/3, 62, 66, 103, 101, 100

[56] References Cited

U.S. PATENT DOCUMENTS

| | | | |
|---|---|---|---|
| 3,593,767 | 7/1971 | Smith | 206/524.8 X |
| 3,749,237 | 7/1973 | Dorton | 206/438 |
| 3,870,150 | 3/1975 | Hummel | 206/438 |
| 3,941,245 | 3/1976 | Oliverius | 206/438 |
| 4,417,658 | 11/1983 | Gardner et al. | 206/438 |
| 4,583,643 | 4/1986 | Sanderson | 206/438 |
| 5,040,904 | 8/1991 | Cornwell | 383/71 |

FOREIGN PATENT DOCUMENTS

| | | | |
|---|---|---|---|
| 0549840 | 12/1957 | Canada | 383/66 |
| 00029750 | 2/1991 | Japan | 206/524.8 |
| 2177677 | 1/1987 | United Kingdom | 383/66 |

Primary Examiner—Bryon P. Gehman
Attorney, Agent, or Firm—Notaro & Michalos

[57] ABSTRACT

A container that will contain contaminated surgical garments is closed after the container is filled to a recommended level, using a closure system that causes the container to become air tight and also will not allow vapors or gases to escape or enter. There is a one way valve for air to be vacuumed from the container but not to return. All the air will be vacuumed from the container making it a small manageable waste package ready for storage or incineration.

11 Claims, 4 Drawing Sheets

CRYPTOPLATE DISPOSABLE SURGICAL GARMENT CONTAINER

BACKGROUND OF INVENTION

The present invention relates to disposable containers, and pertains particularly to a disposable container with vacuum valve means and a securable closure for containment of infectious surgical garments.

The current method of disposing of surgical garments involves the placement of contaminated garments into a container. In the event the container is a bag, when the bag is filled to the recommended level, the bag will be tied for closure which results in air being trapped in the bag. Thus, creating a much larger than needed bag of waste.

SUMMARY OF THE INVENTION

The invention is a disposable surgical garment container comprising a hollow body having a transverse slit near the top for permitting access to the interior of the container body. A predetermined length of polyethylene is attached to the body of the container over the slit for reinforcement. A valve is placed beside the reinforced slit with means of vacuuming the air from the container. A closure is provided extending beneath the reinforced slit for ultimate closure of the container when filled.

The body of the disposable surgical garment container is made from a co-extruded polyethylene film. The film is composed of three (3) layers. The outer layer is a linear low density polyethylene, the sandwich layer is a linear low density polyethylene/low density polyethylene, and the inside layer is a low density polyethylene. All three layers are made from virgin materials with no diarylides or heavy metals. When incinerated it emits no harmful gases and produces a clean ash.

The body of the container will be sealed on the top and the bottom margins of the body. These two seals are transverse air-pocket seals. The seal consists of two master seals and 45 degree angular members between the two master seals creating air pockets for strength and rigidity, thus, creating leak proof seals.

The body also consists of a slit with means for creating an opening to allow for the insertion of the contaminated surgical garments. The slit is reinforced by a strip of polyethylene adhered to the body of the container by a heat melt process. The strip of polyethylene will cover the slit so that when opened there will be no tearing of the body of the container.

The closure system will create a leak proof, air proof closure and will not allow gases, vapors or liquids to be expelled from the slit. The closure consists of a strip of self adhesive polyethylene tape that has a liner (backing). When the container is filled to the recommended level, the liner (backing) will be peeled off and the tape will be placed over the slit for ultimate closure. The strip of self adhesive polyethylene tape is attached beneath the reinforced slit for easy placement to cover the slit for an airtight closure.

This invention also includes a valve for vacuuming the air from the container after the closure has been applied. This valve is a one way, single use valve and will not let air enter, after the vacuuming process has been exercised. The valve is attached to the body of the container in close proximity to the slit, so that when the strip of polyethylene is applied to the slit the valve will also be covered. Although the valve is attached with an adhesive to the body, since the container will not remain flat, the strip of polyethylene helps keep the valve in place.

BRIEF DESCRIPTION OF THE DRAWINGS

FIG. 8 shows that where the needle is placed and air flow when the vacuum is on.

DETAILED DESCRIPTION OF THE DRAWINGS

Figure 1:
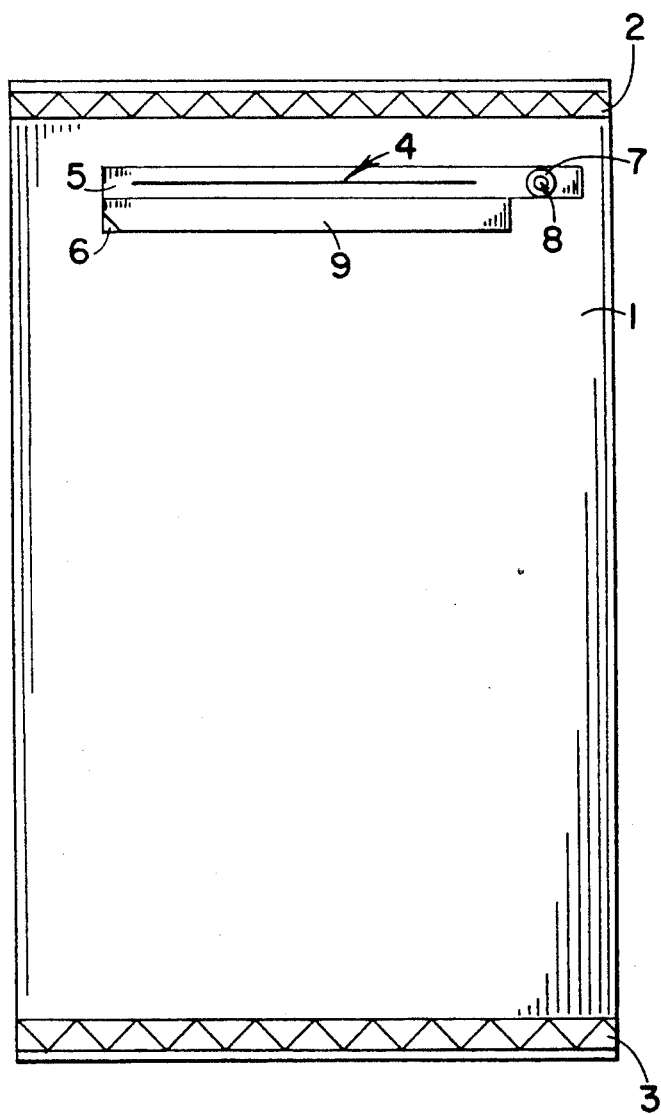
FIG. 1 illustrates the disposable surgical garment container of the invention and all of its components.

The container of the invention is made up of seven important components as shown in FIG. 1. They are; a tubular body of the container 1, an upper seal 2, a lower seal 3, a slit (opening for disposal of garments) 4, reinforcing strip of polyethylene 5, closure tape 6, and a vacuum valve 7. This apparatus is designed to contain, transport, and store infectious medical surgical garments. The most important matter about this apparatus is that while containing, transporting, and disposing it will be a small (space saving) vacuum packed container.

Figure 5:
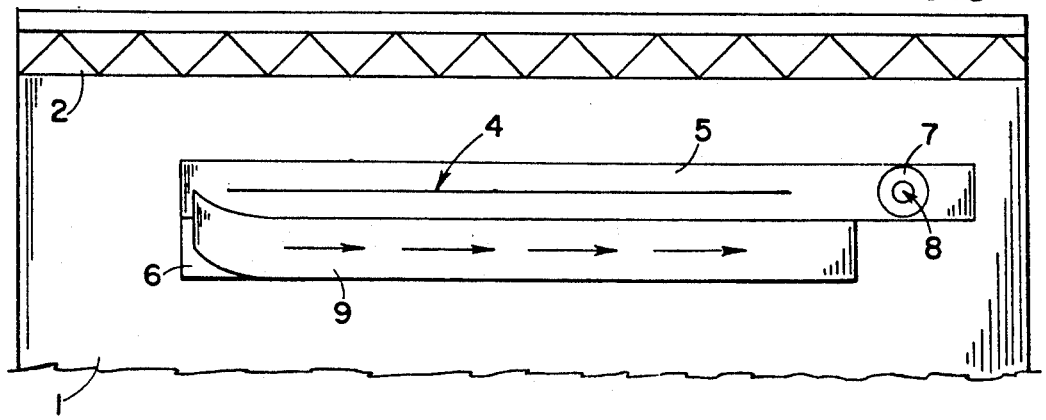
FIG. 5 illustrates the peeling off of the liner(backing) of the closure tape exposing the adhesive.

After the operation is complete the surgeons, anesthesiologists and nurses will disrobe and dispose of the contaminated garments into this apparatus. First by opening the slit that is reinforced with a strip of polyethylene 5, therefore dropping the contaminated garments into the body of the container 1. Secondly, after the body of the container 1 has been filled to the recommended level, the liner (backing) 9 of the closure tape 6 will be peeled off as shown in FIG. 5.

Figure 6:
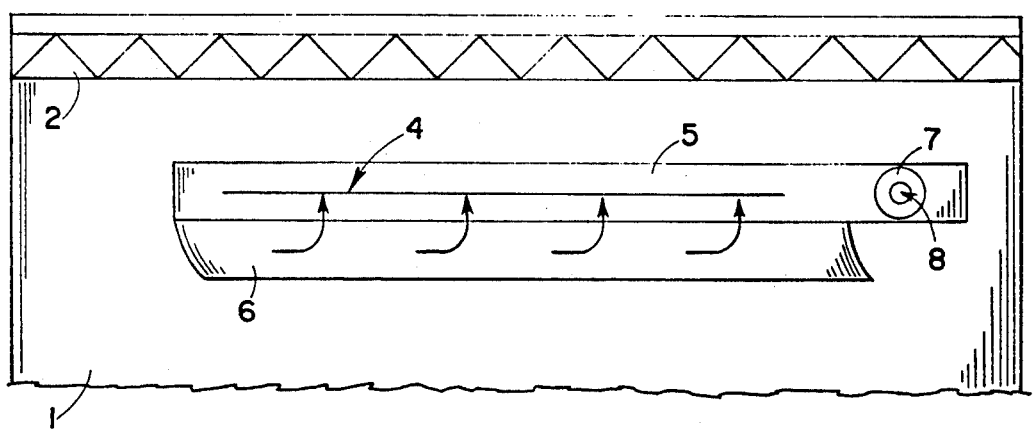
FIG. 6 illustrates the closure tape being placed over the slit.
Figure 7:
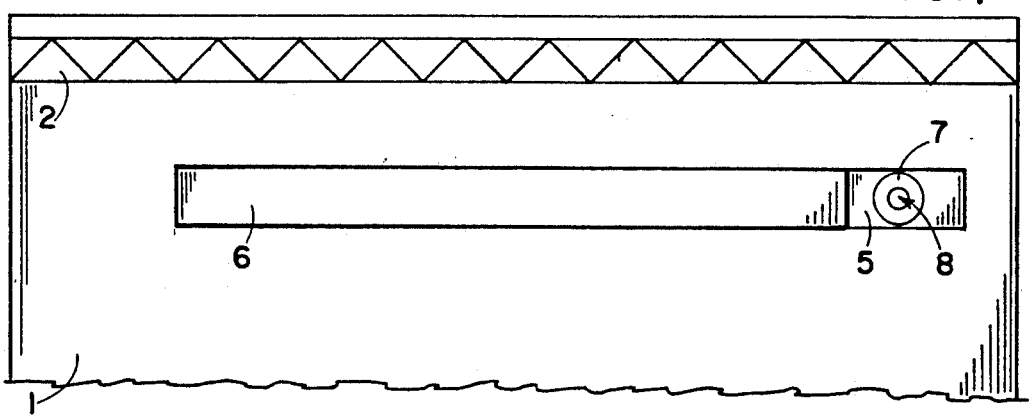
FIG. 7 illustrates the closure tape in place ready for the vacuum process.

Then the closure tape 6 will be folded over the slit 4 (FIG. 6) for ultimate closure (FIG. 7). Thus, producing an air tight and leak proof container with the aid of the upper seal 2 and the lower seal 3.

Figure 2:
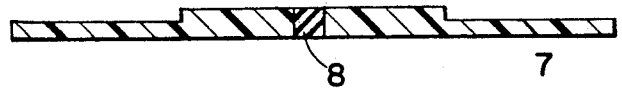
FIG. 2 is a sectional view of the one way vacuum valve.
Figure 3:
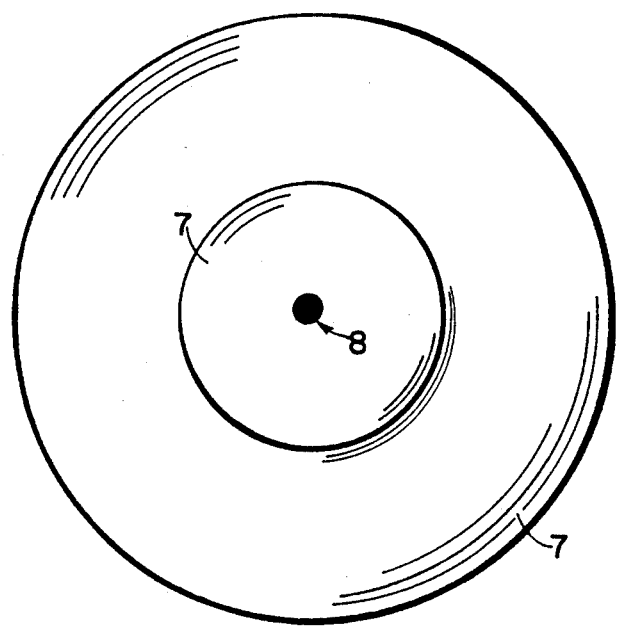
FIG. 3 illustrates the top of the one way vacuum valve.
Figure 4:
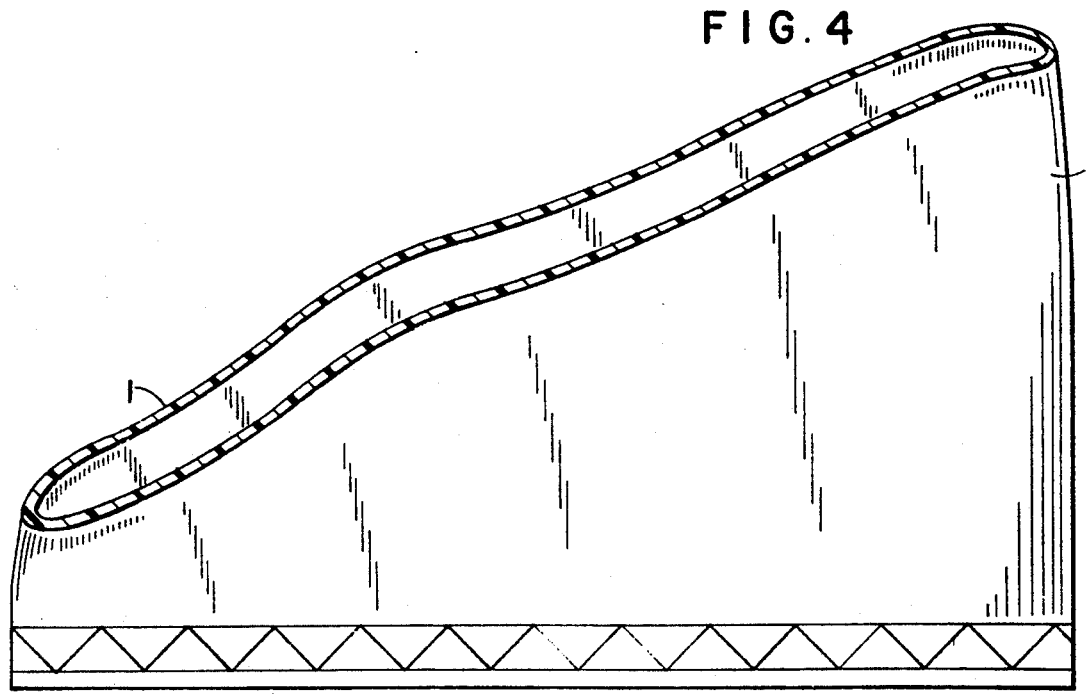
FIG. 4 is a partial view of the container body.
Figure 8:
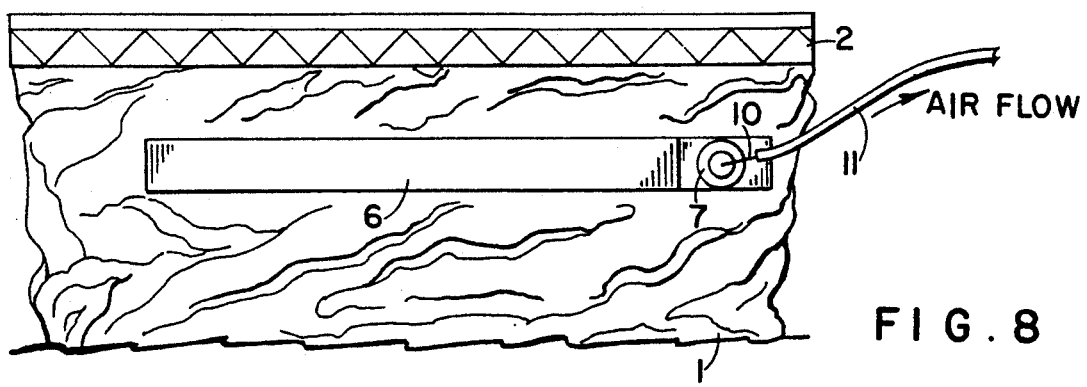
Figure 9:
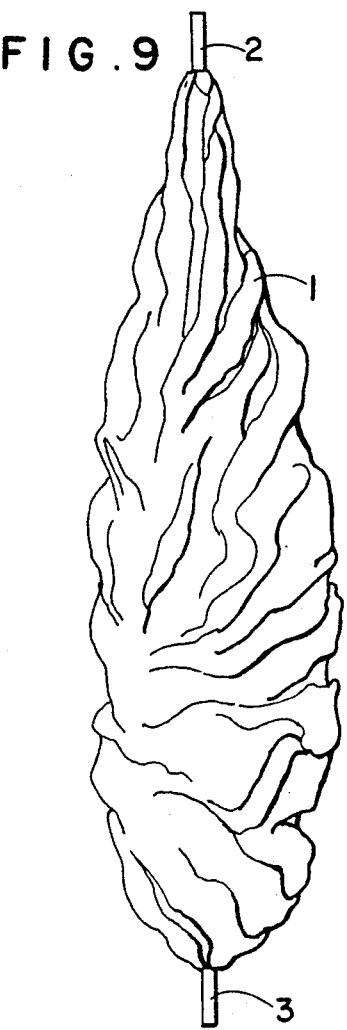
FIG. 9 illustrates a side view of the garment container when filled with infectious medical garments.
Figure 10:
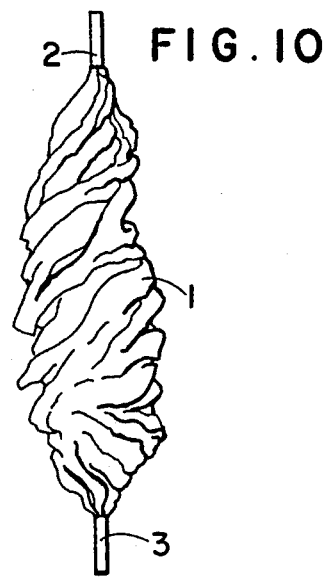
FIG. 10 illustrates a side view of the garment container when filled and vacuumed after closure.

The last step involving this apparatus is the vacuuming of the air from the body of the container as shown in FIG. 8. First, a needle 10 is pushed into the vacuum valve 7 far enough for the air opening to pass through the valve opening 8. Once the vacuum process has begun, the air will be vacuumed from the container through the needle 10 and hose 11. The container will remain in the vacuum state. The apparatus is then much smaller, thus will permit less storage space and fewer transporting trips to the incinerator, therefore saving time, space and money. Opening 8 as shown in FIGS. 2 and 3 is filled with a piercable, self-closing, resilient material so that when needle 10 is removed, the opening closes.

I claim:

1. A container for infectious medical waste comprising:

a container body having an elongated slit therein for receiving infectious medical waste into an interior of the body;

a one-way valve secured to the body near the slit for applying a vacuum to the interior of the container body to remove air from the interior of the container body;

an elongated closure tape for engagement over the slit to close the slit after the container body is filled to a selected level with infectious medical waste and after which air in the container body is removed through the one-way valve; and a reinforcing strip extending along the slit for reinforcing the slit and extending around the valve for helping secure the valve to the container body.

2. A container according to claim 1, where in the valve comprises an opening filled with a piercable, self-closing resilient material.

3. A container according to claim 2, including in combination, a needle for piercing the piercable material and a vacuum hose connected to the needle for use when the needle has pierced the self-closing material to remove air from the container body.

4. A container according to claim 1, wherein the container body is tubular and is made of plastic, the body having upper and lower ends and a side wall between the upper and lower ends, an upper seal closing the upper end of the tubular body, a lower seal closing the lower end of the tubular body, the body having a width on the side wall thereof and the slit extending along at least a portion of the width of the side wall between the upper and lower seals.

5. A container according to claim 4, wherein each of the upper and lower seals comprises a pair of spaced apart transverse master seals and a plurality of angular seal members extending between the master seals to form a plurality of air pockets between the master seals distributed transversely along the upper and lower seals.

6. A container according to claim 5, wherein each air pocket is triangular.

7. A container according to claim 6, wherein the closure tape is connected to the container body and extends parallel to the slit, the closure tape having an adhesive surface facing away from the container body, and a backing covering the adhesive surface and being removable so that the closure tape can be folded over to cover and close the slit.

8. A container for infectious medical waste comprising:

a container body having an elongated slit therein for receiving infectious medical waste into an interior of the body;

a one-way valve secured to the body near the slit for applying a vacuum to the interior of the container body to remove air from the interior of the container body;

an elongated closure tape for engagement over the slit to close the slit after the container body is filled to a selected level with infectious medical waste and after which air in the container body is removed through the one-way valve, the closure tape being connected to the container body and extending parallel to the slit, the closure tape having an adhesive surface facing away from the container body, and a backing covering the adhesive surface and being removable so that the closure tape can be folded over to cover and close the slit; and a reinforcing strip extending along the slit and next to the closure tape for reinforcing the slit, the reinforcing strip extending around the one-way valve.

9. A container according to claim 8, wherein the valve comprises an opening filled with a piercable, self-closing resilient material.

10. A container according to claim 9, wherein the one-way valve comprises a disk sealed to the container body and containing the opening filled with piercable self-closing resilient material.

11. A container according to claim 10, wherein the container body is made of a multilayer polyethylene film, the reinforcing strip being made of polyethylene.

* * * * *